(12) United States Patent
Misra et al.

(10) Patent No.: US 10,330,618 B2
(45) Date of Patent: Jun. 25, 2019

(54) METHOD TO ESTIMATE WATER SATURATION IN ELECTROMAGNETIC MEASUREMENTS

(71) Applicant: Schlumberger Technology Corporation, Sugar Land, TX (US)

(72) Inventors: Siddharth Misra, Austin, TX (US); John Rasmus, Richmond, TX (US); Dean Homan, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 43 days.

(21) Appl. No.: 15/569,094

(22) PCT Filed: Apr. 29, 2016

(86) PCT No.: PCT/US2016/029993
§ 371 (c)(1),
(2) Date: Oct. 25, 2017

(87) PCT Pub. No.: WO2016/176541
PCT Pub. Date: Nov. 3, 2016

(65) Prior Publication Data
US 2018/0113088 A1    Apr. 26, 2018

Related U.S. Application Data

(60) Provisional application No. 62/154,944, filed on Apr. 30, 2015.

(51) Int. Cl.
*G01N 27/04* (2006.01)
*G01V 3/26* (2006.01)
*G01V 3/38* (2006.01)

(52) U.S. Cl.
CPC ............. *G01N 27/048* (2013.01); *G01V 3/26* (2013.01); *G01V 3/38* (2013.01); *Y02A 90/344* (2018.01)

(58) Field of Classification Search
CPC ............. G01V 3/38; G01V 3/26; G01V 1/50
See application file for complete search history.

(56) References Cited

U.S. PATENT DOCUMENTS

2004/0164735 A1    8/2004    Hurlimann et al.
2006/0085135 A1    4/2006    Clavaud
(Continued)

FOREIGN PATENT DOCUMENTS

CN    103149220 A    6/2013
RU    2282178 C1    8/2006
(Continued)

OTHER PUBLICATIONS

International Search Report and Written Opinion issued in International Patent application PCT/US2016/029993, dated Sep. 1, 2016. 11 pages.
(Continued)

*Primary Examiner* — Giovanni Astacio-Oquendo
*Assistant Examiner* — Alvaro E Fortich

(57) ABSTRACT

A method to estimate water saturation in electromagnetic measurements includes making an electromagnetic measurement and performing at least one of (a) creating an analytical forward model of the EM measurement, (b) creating a numerical finite difference forward model of the EM measurement, and (c) performing an inversion. The method also includes removing at least one petrophysically-adverse alteration of EM measurements in the frequency range from 1 Hz to 100 MHz. A petrophysically-adverse
(Continued)

10μm-radius spherical inclusions or vugs.
Volume fraction = 5% alteration is due to the presence of at least one of the following: pyrite, graphitic-precursors, magnetite, and other conductive minerals.

8 Claims, 15 Drawing Sheets

(56) References Cited

U.S. PATENT DOCUMENTS

| | | | |
|---|---|---|---|
| 2006/0136135 A1* | 6/2006 | Little | G01V 11/00 |
| | | | 702/13 |
| 2010/0017132 A1 | 1/2010 | Glinisky et al. | |
| 2010/0185393 A1* | 7/2010 | Liang | G01V 3/28 |
| | | | 702/7 |
| 2010/0185422 A1 | 7/2010 | Hoversten | |
| 2012/0293179 A1* | 11/2012 | Colombo | G01V 3/26 |
| | | | 324/339 |
| 2013/0241561 A1 | 9/2013 | Allen | |

FOREIGN PATENT DOCUMENTS

| | | |
|---|---|---|
| WO | WO2014000758 A1 | 1/2014 |
| WO | WO2014165478 A1 | 10/2014 |
| WO | 2016081669 A1 | 5/2016 |

OTHER PUBLICATIONS

Schwarz, Gerhard. A theory of the low-frequency dielectric dispersion of colloidal particles in electrolyte solutionl, 2. The Journal of Physical Chemistry,66(12), 2636-2642. 1962.

Dukhin et al., Dielectric Phenomena and Double Layer in Disperse Systems and Polyelectrolytes. Journal of the Electrochemical Society, 121(4), 154C-154C. 1974.

Grosse et al., Permittivity of a suspension of charged spherical particles in electrolyte solution. Journal of Physical Chemistry,91(11), 3073-3076. 1987.

Grosse et al., The influence of diffusion on the dielectric properties of suspensions of conductive spherical particles in an electrolyte. Journal of Physics D: Applied Physics, 25(3), 508. 1992.

Wong, J., An electrochemical model of the induced-polarization phenomenon in disseminated sulfide ores. Geophysics, 44(7), 1245-1265. 1979.

Chu et al., Nonlinear electrochemical relaxation around conductors. Physical Review E, 74(1), 011501. 2006.

Schmuck et al., Homogenization of the Poisson-Nernst-Planck equations for ion transport in charged porous media. arXlv preprint arXiv:1202.1916. 2012.

Anderson et al., Identifying Potential Gas-Producing Shales From Large Dielectric Permittivities Measured by Induction Quadrature Signals, SPWLA 49th Annual Logging Symposium held in Edinburgh, Scotland, May 25-28, 2008, 10 pages.

Misra et al., Interfacial polarization of disseminated conductive minerals in absence of redox-active species—Part 1: Mechanistic model and validation, Geophysics, vol. 81, No. 2, Mar. 1, 2016, pp. E139-E157.

Wang et al., The Broadband Electromagnetic Dispersion Logging Data in a Gas Shale Formation: A Case Study, SPWLA 54 th Annual Logging Symposium, Jun. 22, 2013, 12 pages.

Anderson et al., Observations of Large Dielectric Effects on Induction Logs, or Can Source Rocks Be Detected with Induction Measurements, 47th Annual Logging Symposium held in Veracruz, Mexico, Jun. 4-7, 2006, 12 pages.

* cited by examiner

10μm-radius spherical inclusions or vugs.
Volume fraction = 5%

10μm-radius discs
Volume fraction = 0.7%

0.833μm-thick beds or fractures.
Volume fraction = 5%

3.64μm-radius veins
Volume fraction = 5%

METHOD TO ESTIMATE WATER SATURATION IN ELECTROMAGNETIC MEASUREMENTS

CROSS-REFERENCE TO RELATED APPLICATIONS

The present application claims priority to U.S. Provisional Application 62/154,944 filed Apr. 30, 2015, the entirety of which is incorporated by reference.

FIELD OF THE INVENTION

Aspects relate to water saturation in geological environments. More specifically, aspects relate to methods to estimate water saturation in electromagnetic measurements.

BACKGROUND

Conventional interpretation of electromagnetic measurements in heterogeneous materials neglects electrodiffusion and electrochemical effects occurring at interfaces. Such neglect of electrodiffusion and electrochemical effects may grow significant at the interfaces of, for example, geological stratum. As a result of this neglect, interpretations may be inaccurate, causing skewed results. For recovery of hydrocarbons, for example, such inaccuracies can seriously impact the economic viability of recovery of hydrocarbons from wellbores.

SUMMARY

The following summary does not limit the overall scope of the application. In one non-limiting embodiment, a method to estimate water saturation in electromagnetic (EM) measurements is disclosed having making an electromagnetic measurement, performing at least one of creating an analytical forward model of the EM measurement, creating a numerical finite difference forward model of the EM measurement, performing an inversion, removing at least one petrophysically-adverse alteration of EM measurements in the frequency range from 1 Hz to 100 MHz and wherein the at least one petrophysically-adverse alteration is due to the presence of at least one of the following: pyrite, graphitic-precursors, magnetite, and other conductive minerals.

Other aspects and advantages of the claimed subject matter will be apparent from the following description and the appended claims.

DETAILED DESCRIPTION

Figure 1:
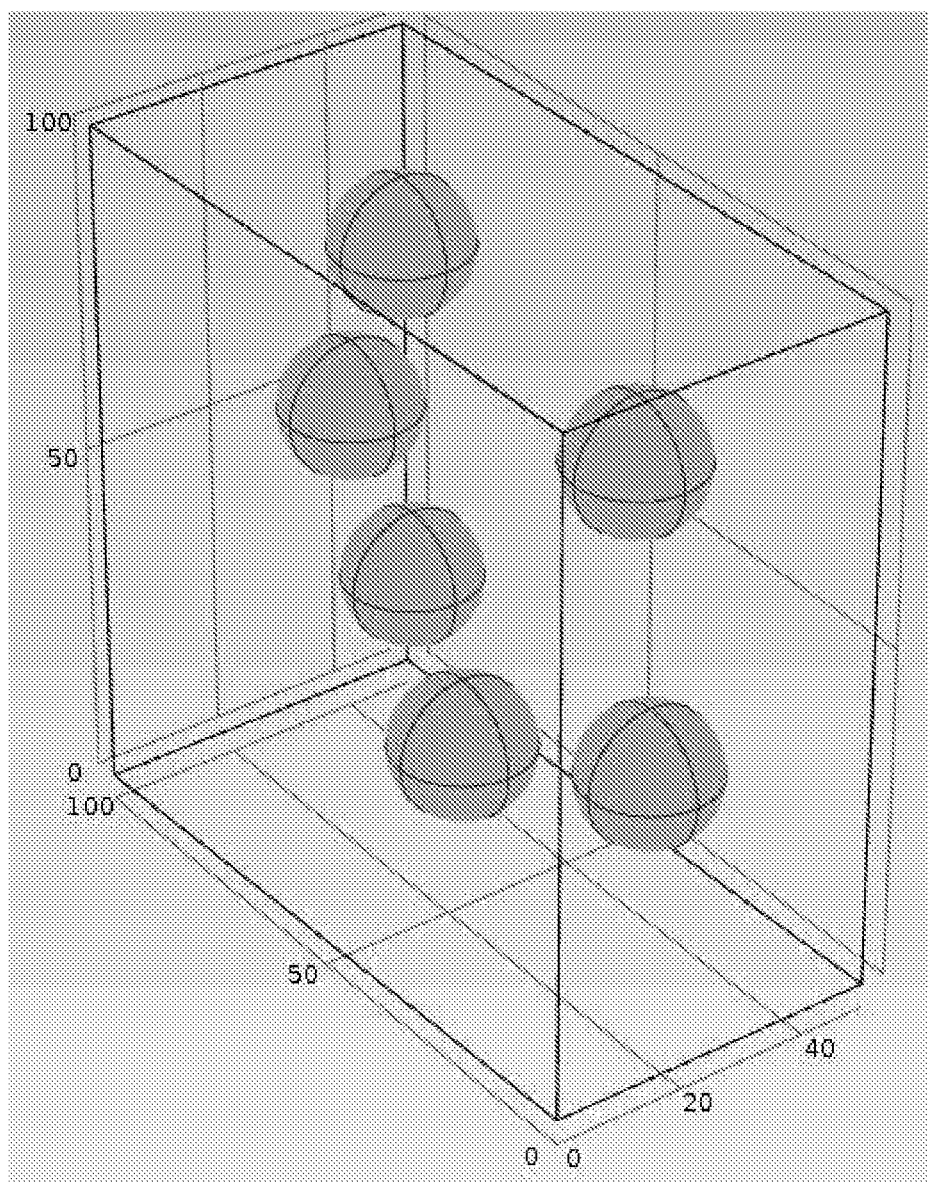
FIG. 1 is a model of a porous geological material as disclosed herein where dispersed phases do not interact with one another.
Figure 2:
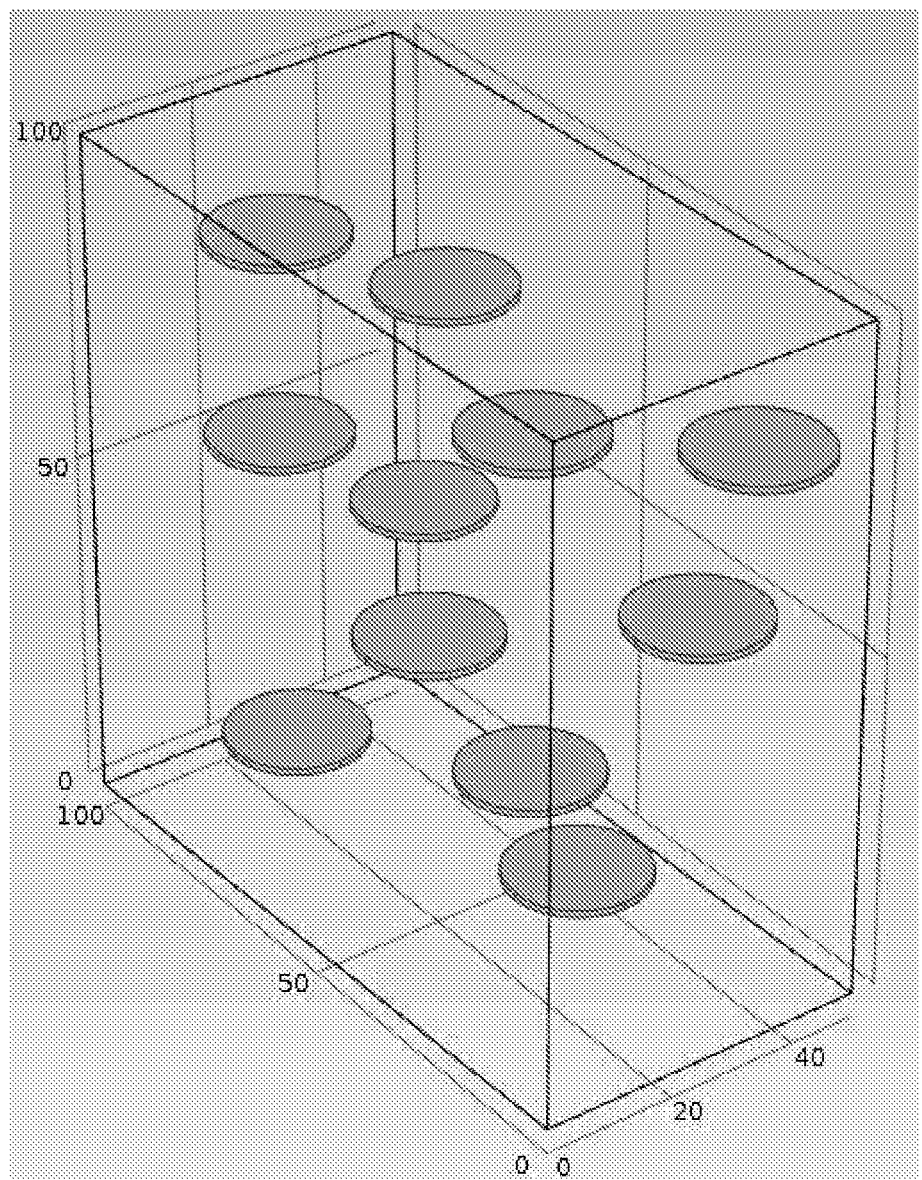
FIG. 2 is a model of a porous geological material as disclosed herein where dispersed phases do not interact with one another.
Figure 3:
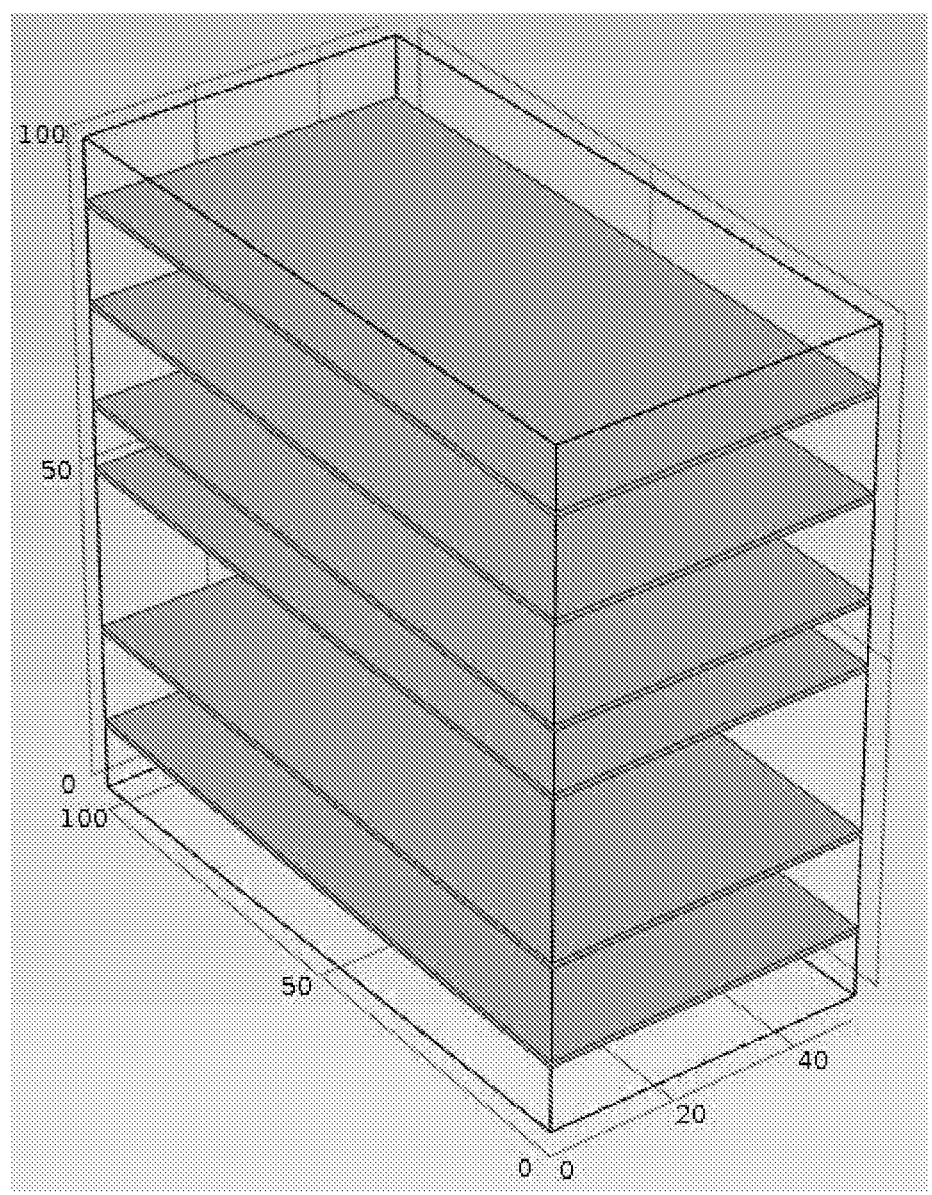
FIG. 3 is a model of a porous geological material as disclosed herein where dispersed phases do not interact with one another.
Figure 4:
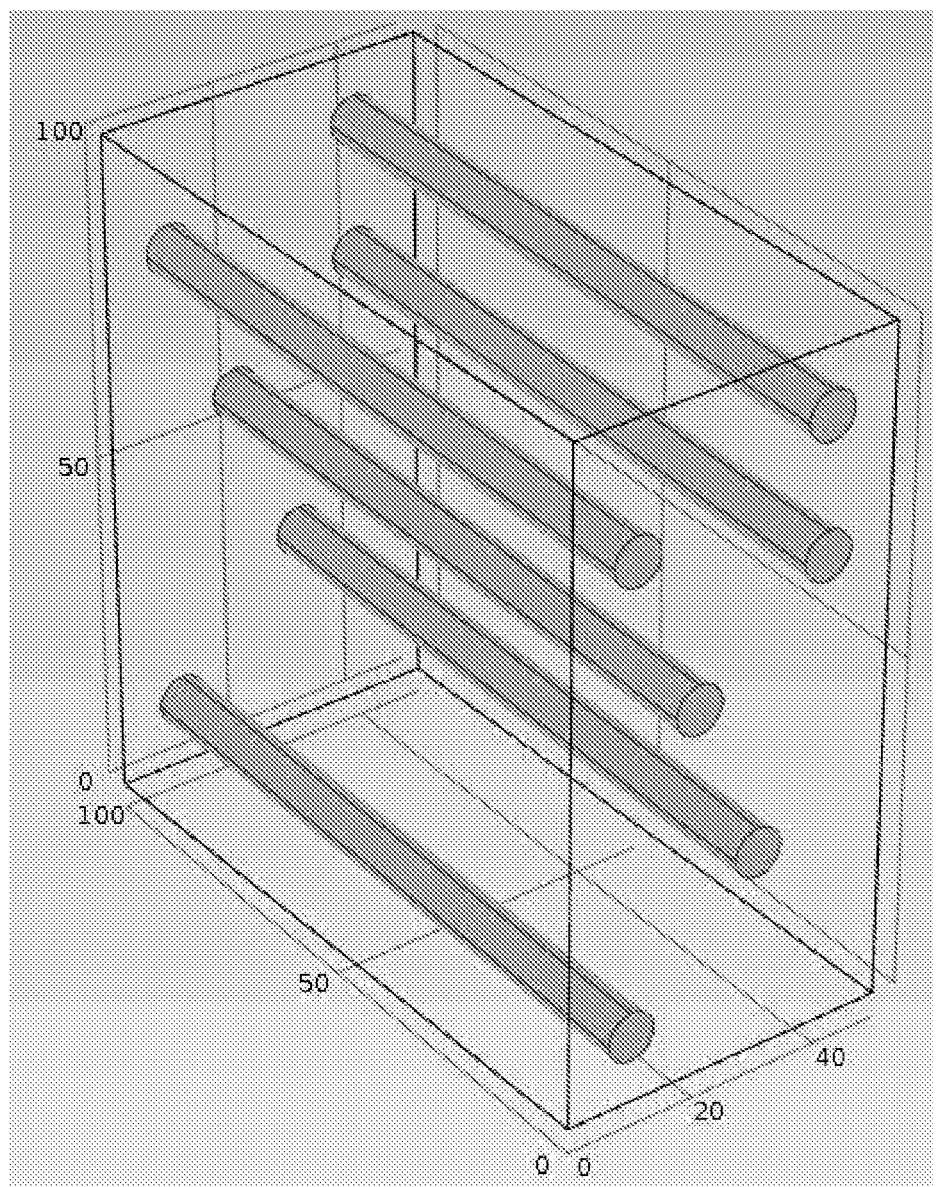
FIG. 4 is a model of a porous geological material as disclosed herein where dispersed phases do not interact with one another.
Figure 5:
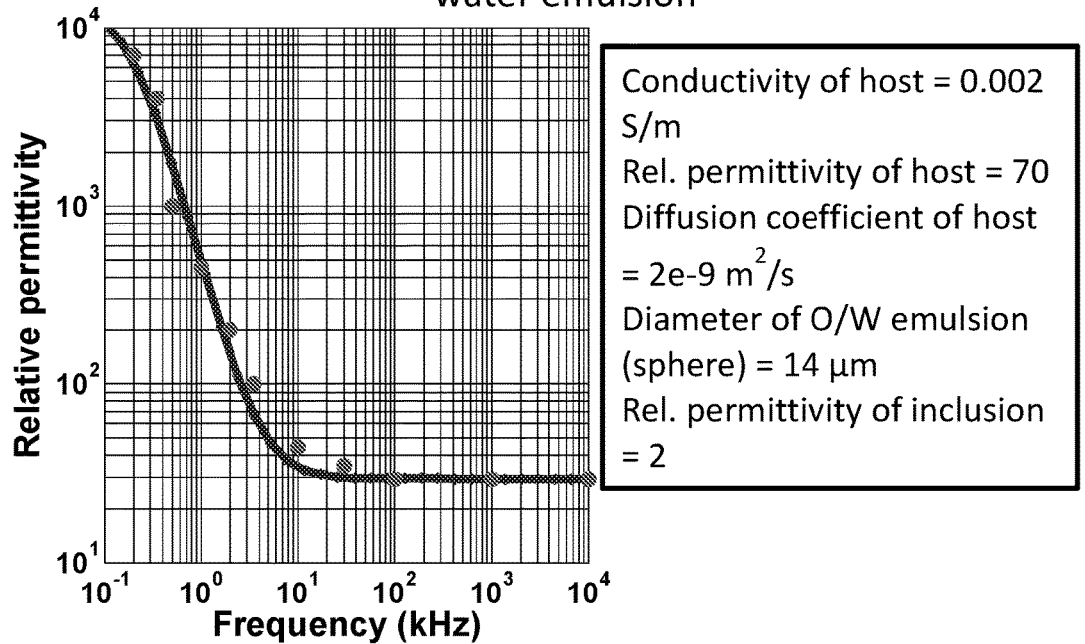
FIG. 5 is a graph for a dispersed highly-conductive spherical inclusion in an electrolyte-filled porous conductive medium.
Figure 6:
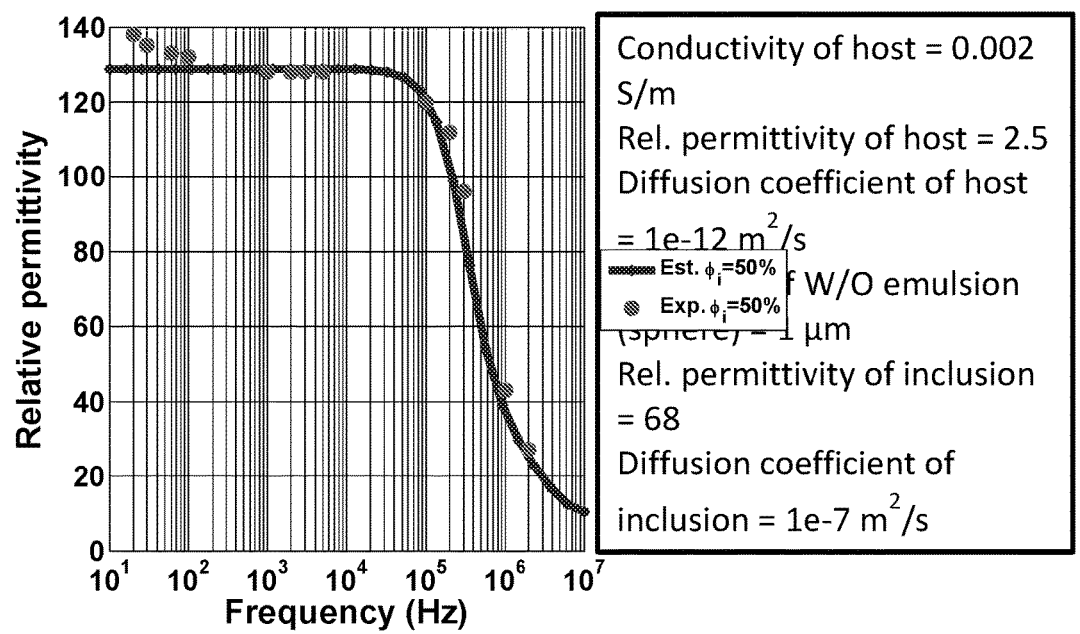
FIG. 6 is a graph for a dispersed highly-conductive spherical inclusion in an electrolyte-filled porous conductive medium.
Figure 7:
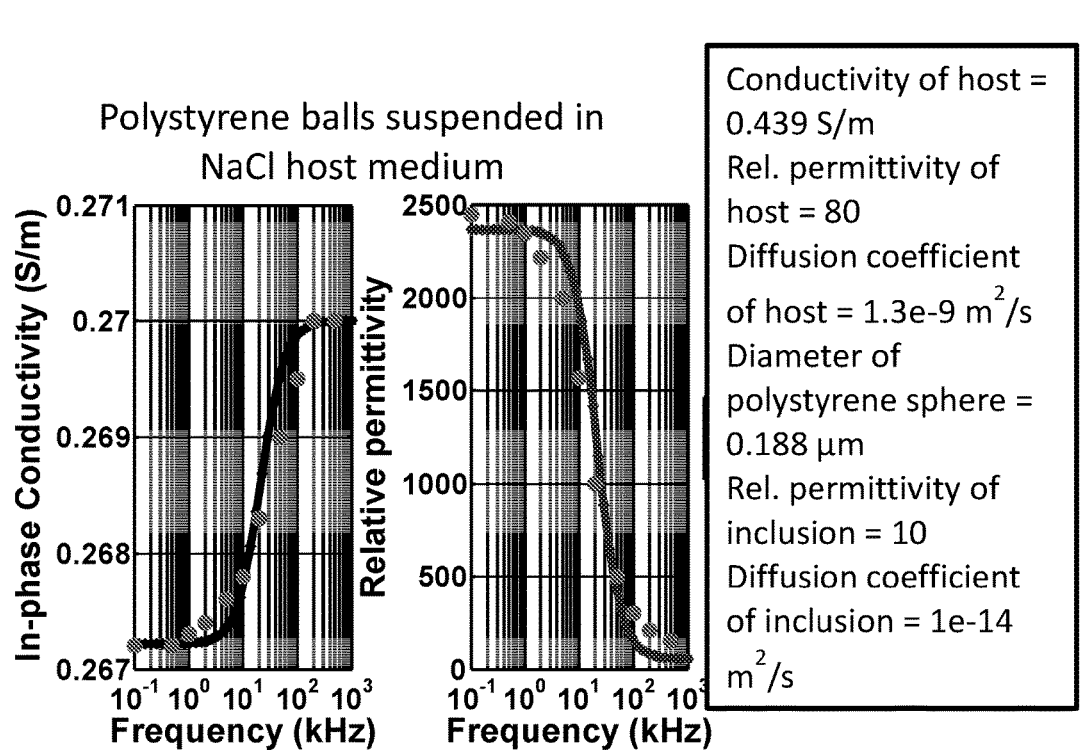
FIG. 7 shows a graph for a dispersed highly-conductive spherical inclusion in an electrolyte-filled porous conductive medium.
Figure 8:
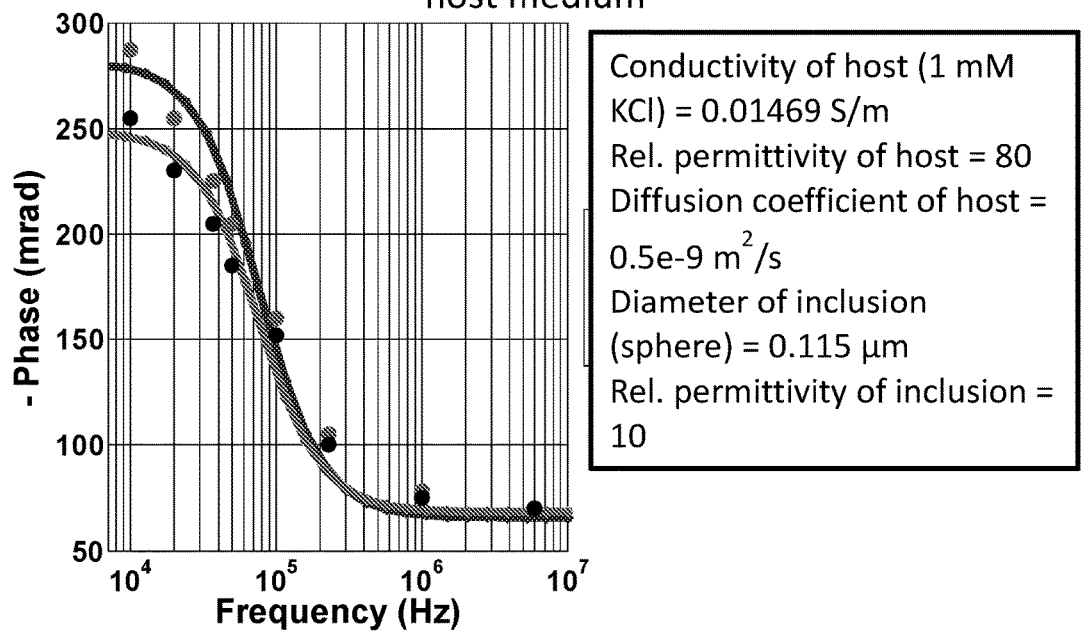
FIG. 8 shows a graph for a dispersed highly-conductive spherical inclusion in an electrolyte-filled porous conductive medium.
Figure 9:
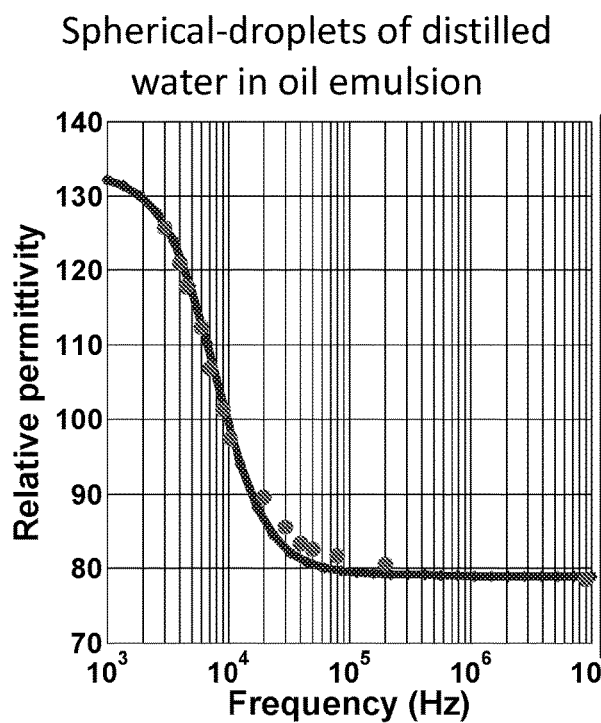
FIG. 9 shows a graph for a dispersed highly-conductive spherical inclusion in an electrolyte-filled porous conductive medium.
Figure 10:
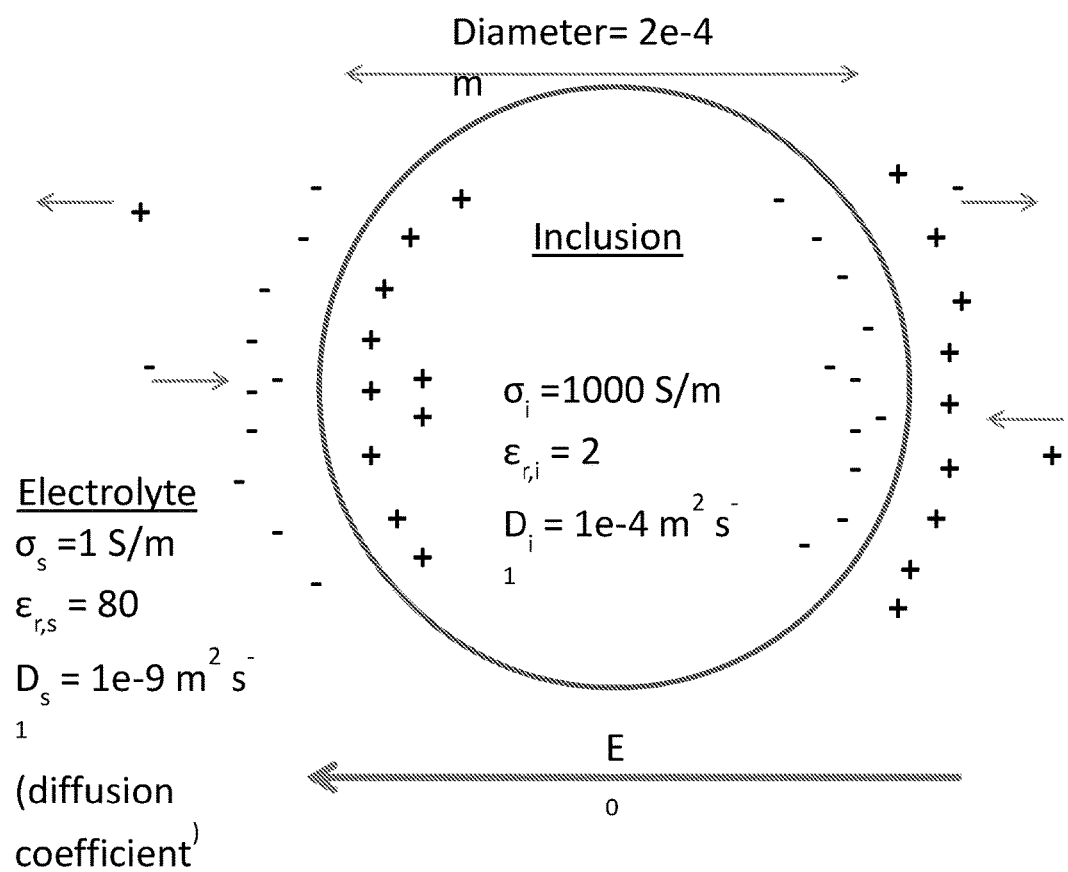
FIG. 10 shows a model for a dispersed highly-conductive spherical inclusion in an electrolyte-filled porous conductive medium.

It is proposed that effects of interfacial polarization on electromagnetic measurements in heterogeneous and anisotropic geological formations should be quantified in order to accurately estimate electrical properties of the host as well as the dispersed phase. Electromagnetic response of a porous geological material is affected by the presence of inclusions, vugs, veins, fractures, and thin-beds. In one non-limiting embodiment an analytical and numerical model of the interfacial polarization of a porous geological material containing dispersed phase to identify and quantify the interfacial polarization effects on complex conductivity response is disclosed. In the analytical model, a dipole moment is determined due to a single, isolated dispersed phase. Then a consistent effective medium formulation is used to determine effective complex conductivity of the geological mixture. Based on the prior knowledge of type of dispersed phase, an inversion algorithm is used to estimate the volume fraction of the dispersed phase and conductivity of the host medium or dispersed phase depending upon the requirement. Also, these models facilitate the used to understand the sensitivity of complex conductivity response to various electromagnetic petrophysical properties over a wideband frequency range (kHz-MHz). Petrophysical applications of the proposed invention may be used to: quantify the MIP effects of conductive mineral inclusions, such as pyrite and graphite, for improving resistivity interpretation of induction and dielectric measurements; quantify the MIP effects of conductive thin beds for improving resistivity interpretation of induction and dielectric measurements; quantify the MIP effects of conductive veins for improving resistivity interpretation of induction and dielectric measurements; quantify the MIP effects of parallel fractures for improving resistivity interpretation of induction and dielectric measurements; in conjunction with other petrophysical measurements, estimate volume fraction and the geometry of conductive minerals for applications in petrology, paleogeology, and paleothermometry; and/or improve resistivity interpretation in formations containing isolated vuggy porosity One or more specific embodiments of the present disclosure are described below. These embodiments are merely examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts might be complex and time consuming, but would nonetheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features.

As defined herein, interfacial polarization refers to the external field-driven accumulation of charge carriers at the phase boundaries in geological mixtures. Dynamics of charge carriers (diffusion and electromigration) on both sides of the interface affects the electromagnetic (EM) response of the geological mixture. Pyrite-bearing sedimentary rocks and graphite-bearing thermogenic source rocks demonstrate MIP phenomena in an external electric field. A mechanistic model of interfacial polarization in geological mixture has been developed, as a non-limiting embodiment, based on Poisson-Nernst-Planck (PNP) equations for dilute solution in a weak electrical field. PNP equations are more realistic compared to circuit models that reduce transport problems of electrokinetics to electrostatic problem based on the assumption that the bulk concentration remains uniform at all times. The relationship of characteristic frequency of the dispersion curve is investigated and of static relative permittivity of the geological mixture to the dimensions, electrical properties, and volume fraction of the individual elements of the dispersed phase. Contrary to conventional literature, a strong dependence of complex conductivity response of a geological mixture has been found to the conductivity of the host medium.

Analytical Model

Modeling of interfacial polarization can be done using circuit models, empirical models, phenomenological models, or mechanistic models. A physically consistent model must satisfy Kronig-Kramers relationship. Many analytical models are built for cases when dispersed phase don't interact with each other. As a result, a single element is analyzed followed by applying an effective medium formulation to the entire mixture. An interfacial polarization mechanism has been modeled as a diffusion of counterions moving along the surface of the particle. This modeling framework neglects all bulk diffusion effects by calculating the potential outside the counterion layer as a solution to laplace equation rather than poisson's equation. Another approach to this problem is based on the concept of a diffused double layer. Non-linearity of this equation leads to extreme mathematical complexity which does not provide analytical expressions for relaxation parameters. A simplified model was developed which leads to an analytical solution for interfacial polarization for charged spherical particles in electrolyte solution. Another approach to analyze the effects of interfacial polarization in various hydrocarbon-bearing geological formations has been developed. In an external field, the charge carriers in the dispersed phase migrate and accumulate at the impermeable interface. Consequently, the dispersed phase behaves as dipoles in presence of electric field. Additionally, the charge carriers in the host medium migrate under the influence of external electric field and accumulate on the interface resulting in substantial dielectric enhancement. Taylor-series simplification is not applied to the effective medium formulation in order to account for the large reflection coefficient or dipolar coefficient that develops due to the interfacial polarization.

Numerical modeling work on dielectric enhancement and conductivity dispersion was not found relevant due to interfacial polarization. Inversion algorithm coupled to an analytical modeling was not found relevant.

The aim of this model is to describe the complex conductivity response of host medium, representing a porous geological material, containing small volume fraction of conductive phase, which can be a inclusion, vug, vein, fracture, or beds. Configurations are represented in FIGS. 1-4, wherein the dispersed phase don't interact with each other. As a result, a single element for each of the configurations can be analyzed. Linear response to weak field where exact solutions are possible are considered. In absence of an external field, a Guoy-Chapman regime and negligible surface charge on dispersed phase is assumed. Thus, an extremely thin double layer exists around the surface of conductive dispersed phase and negligible surface conductivity, which is similar to the assumptions made in electrochemistry and colloid science with respect to electrochemical relaxation around metallic surfaces. Also, absence of redox active species and influence of pH of pore water are assumed. As a result, the interface acts as an impermeable layer to the transport of charge carriers from one phase into the other. Further, the volume fraction of dispersed phase is less than 0.15, as a result the individual elements of the dispersed phase are not contact with each other and there is no electromagnetic coupling between them. The host and the dispersed phase can be modeled as a conductive, insulating, or dielectric material that has negligible frequency dependence. Therefore, the large frequency dependence of complex conductivity of geologically-complex formations results from the occurrence of interfacial polarization. Conductive dispersed phase act as an insulator at low frequencies and as a high conductive path at high frequencies. Analytical modeling results show that the frequency dependence of interfacial polarization effects is controlled by relaxation time that strongly depends on the shape of the dispersed phase and the diffusion coefficient of charge carriers. In microscopic continuum models of charge transport in electrolytes, the charge carrier fluxes are given by Nernst-Planck equations describing diffusion and electromigration in the mean electric field, which is determined self-consistently from the mean charge density via Poisson's equation. PNP model has been applied to electrolytes as well as semiconductors, where electrons and holes behave like anions and cations, respectively. Poisson equation is applied to describe the electric field in terms of electrostatic potential, whose gradient governs electromigration. The Nernst-Planck (NP) equation is used to describe the electrodiffusion of ions in terms of ion concentration. Limitation of PNP equations arises from the omission of the finite volume effect of ion particles, ion-ion interaction and steric effects, transport of ion in confined channels, and correlation effects. In order to estimate the complex conductivity response of a geological mixture, the response of an isolated element surrounded by host medium is evaluated when subjected to a uniform, applied electric field. In order to simplify analytical complexity of the model, the focus is on symmetric, binary charge carriers in both the host medium and dispersed medium, thus the charge species in any given phase have the same diffusivity and charge number. However, the diffusivity and charge numbers of the charge carriers in the dispersed phase are different compared to that for the host medium. Also, for simplicity, we perform most of our analysis for dilute, completely dissociated, binary, symmetric systems. For concentrated media, chemical potential of a charge carrier increases beyond that of dilute media due to various physical effects.

PNP Model Formulation

At $t<0$, no external voltage is applied, it is assumed there is no spontaneous accumulation of charges on the interface.

For low frequencies $\ll \frac{a^2}{\lambda_D^2}$, where $$\text{Debye screening length} = \lambda_D = \sqrt{\frac{\varepsilon_s kT}{2Z^2 e^2 N_0}}$$

Under weak field approximation, such that $|c_j^\pm| \leq N_{0j}^\pm$, an external electric field $E=E_0 e^{-j\omega t}$ results in perturbation of ionic charge densities and potentials near the interface from its equilibrium condition:

$$N_j^\pm = N_{0j}^\pm + c_j^\pm(r) e^{-j\omega t} \cos(\theta)$$

Subscript for host medium=s
Subscript for dispersed medium=i
r is the distance along the normal to the interface.
$\theta$ is the angle between incident electric field and the normal to the interface.
$c_j^\pm$ is the ion density variation due to electric field near the interface.
Charge carrier density in the medium, j, without an external field=$N_{0j}^\pm$
Mobility of charge carrier in the medium, $j=\mu_j^\pm$
Charge number of charge carrier in the medium, $j=Z_j^\pm$
The simplified assumption is that both of the media are binary and symmetric with respect to charge carrier:

$$Z_j^\pm = 1;\ \mu_s^+ = \mu_s^- = \mu_s;\ \mu_i^+ = \mu_i^- = \mu_i;\ N_{0i}^+ = N_{0i}^- = N_{0i};\ N_{0s}^+ = N_{0s}^- = N_{0s}$$

Conductivity of the medium, $j = \sigma_j = 2 N_{0j} \mu_j e$
Complex conductivity of the medium, $j = K_j = \sigma_j + i\omega \varepsilon_j$
Continuity equation for charge carrier density based on mass conservation for each type of charge carriers, $$e \frac{\partial N_j^\pm}{\partial t} = \nabla J_j^\pm \quad 1$$

-continued $$e \frac{\partial N_j^\pm}{\partial t} = ie\omega c_j^\pm$$

Adding both the equations mentioned in 1 gives $$ie\omega d_j = \nabla(J_j^+ + J_j^-) = 2e^2 N_{0j} \mu_j d_j / \varepsilon_j e D_j d_j$$

which can be written as $$d_j = \left(\frac{i\omega}{D_j} + \frac{\sigma_j}{\varepsilon_j D_j}\right) d_j \quad 2$$

where $\sigma_j = 2 N_{0j} \mu_j e$ and $\varepsilon_j = \varepsilon_{rj} \varepsilon_0$; $D_j = \mu_j kT/e$
In equation 2, $$\gamma^2 = \left(\frac{i\omega}{D_j} + \frac{\sigma_j}{\varepsilon_j D_j}\right)$$

Current density of each charge carrier type in each medium is a sum of current density due to drift current and diffusion current. Also, there is no generation/recombination reactions. Then, the transport equation representing conservation laws for ionic species can be written as—

$$J_j^\pm = J_{j,drift}^\pm + J_{j,diffusion}^\pm = eN_j^\pm \mu_j \bar{E}_j$$
$$eD_j \nabla N_j^\pm = eN_j^\pm \mu_j \nabla \varphi_j eD_j \nabla N_j^\pm$$

Where $\varphi_j$ is electric potential and $\bar{E}_j = \nabla \varphi_j$
Diffusivity of charge carrier in medium, $j = D_j = \mu_j kT/e$
where k is the Boltzmann's constant and T is absolute temperature
This gives Nernst-Planck equation $$\frac{\partial N_j^+}{\partial t} = \nabla \left(D_j \nabla N_j^+ + \frac{eD_j}{kT} N_j^+ \nabla \varphi_j\right) \quad 3$$

$$\frac{\partial N_j^-}{\partial t} = \nabla \left(D_j \nabla N_j^- - \frac{eD_j}{kT} N_j^- \nabla \varphi_j\right) \quad 4$$

Distribution of charges within a medium leads to an electric potential, $$\varphi_j(r,\theta,t) = \varphi_j(r) e^{-j\omega t} \cos(\theta)$$

Using Gauss's law, $\nabla(\varepsilon_j \bar{E}_j) = \rho_{f,j} = e(N_j^+ - N_j^-) = e(c_j^+ - c_j^-)$ $$\nabla(\varepsilon_j \bar{E}_j) = \nabla(\varepsilon_j \nabla \varphi_j) = \varepsilon_j \varphi_j$$

$$d_j = (c_j^+ - c_j^-)$$

$$\varphi_j = e d_j / \varepsilon_j \quad 5$$

Equation 3, 4, and 5 together are called the PNP equations.

Combining equation 5 and 2

$$\left(\varphi_j + \frac{e d_j}{\gamma_j^2 \varepsilon_j}\right) = 0 \quad 6$$

If $\in$ is expressed $\in = \varphi_j + \frac{e d_j}{\gamma_j^2 \varepsilon_j}$ then $\in = 0$ \quad 7

Boundary Conditions

The interface is ideally polarizable or completely blocking without any faradic processes, so fluxes of charge carrier vanish on both sides of the interface, respectively.

BC1—Electric potential must be continuous at the interface assuming a zero intrinsic capacitance of interface. This capacitance may represent a stern layer of polarized solvent molecules and/or dielectric coating on the interface.

BC2—The normal component of the displacement component must be continuous at the interfaces. This corresponds to the fact that when diffusive effects are considered no surface charge distribution can occur.

BC3—The normal component of the current density must vanish at the interface. This condition expresses the fact that since no surface charge distribution can buildup, diffusive and electromigrative currents must cancel each other at the interface. Ideally polarizable or completely blocking interfaces without faradic processes are considered, so ionic fluxes have to vanish on the interface.

Effective Medium Formulations $$\frac{K_{\hat{n},eff}}{K_{\hat{n},eff}} \frac{K_s}{N_{\hat{n}} K_s} = \phi_i \frac{K_i}{K_i} \frac{K_s}{N_{\hat{n}} K_s}$$

$$\frac{K_{\hat{n},eff}}{K_{\hat{n},eff}} \frac{K_s}{N_{\hat{n}} K_s} = \phi_i f(\omega)$$

where $K_{\hat{n},eff}$ is effective complex conductivity of the geological mixture.

$$N_{\hat{n}} = \frac{1}{L_{\hat{n}}} \frac{L_{\hat{n}}}{}$$

$L_{\hat{n}}$ is the depolarization factor based on the shape of the dispersed phase.

$\hat{n}$ is the direction of electrical measurement.

For thin beds and induced fractures:

$$f(\omega) = \left(1 - \frac{K_s}{K_i}\right) + \frac{i}{\omega a}\left[\frac{K_s}{K_i} \frac{\sigma_i}{\varepsilon_i} \frac{F_i}{H_i} - \frac{\sigma_s}{\varepsilon_s} \frac{E_s}{G_s}\right]$$

$L_{\hat{x}} = L_{\hat{y}} = 0; L_{\hat{z}} = 1$ $N_{\hat{x}} = N_{\hat{y}} = \infty; N_{\hat{z}} = 0$ For cylindrical veins and natural fractures:

$$f(\omega) = 1 + \frac{2i\omega}{\left[\frac{1}{a}\frac{K_s}{K_i}\frac{\sigma_i}{\varepsilon_i}\frac{F_i}{H_i} - \frac{1}{a}\frac{\sigma_s}{\varepsilon_s}\frac{E_s}{G_s} + i\omega\left(\frac{K_s}{K_i}+1\right)\right]}$$

$L_{\hat{x}} = 0; L_{\hat{y}} = L_{\hat{z}} = \frac{1}{2}$ $N_{\hat{x}} = \infty; N_{\hat{y}} = N_{\hat{z}} = 1$ For spherical inclusions and vugs:

$$f(\omega) = \frac{1}{2} + \frac{3}{2}\frac{i\omega}{\left[\frac{2}{a}\frac{\sigma_s}{\varepsilon_s}\frac{E_s}{G_s} - \frac{2}{a}\frac{K_s}{K_i}\frac{\sigma_i}{\varepsilon_i}\frac{F_i}{H_i} + i\omega\left(\frac{2K_s}{K_i}+1\right)\right]}$$

$L_{\hat{x}} = L_{\hat{y}} = L_{\hat{z}} = \frac{1}{3}$ $N_{\hat{x}} = N_{\hat{y}} = N_{\hat{z}} = 2$ Numerical Model A numerical model was developed using COMSOL AC/DC module to simulate the effect of interfacial polarization due to randomly distributed dispersed phase in a host medium.

Inversion Algorithm

An inversion scheme based on Gauss-Newton minimization was developed for the purposes of estimating volume fraction of conductive mineral inclusions, such as pyrite and graphite, for paleothermometry and improving resistivity interpretation; estimating volume fraction of conductive thin beds for improving resistivity interpretation of induction and dielectric measurements; estimating volume fraction of conductive veins for improving resistivity interpretation of induction and dielectric measurements; estimating volume fraction of parallel fractures for improving resistivity interpretation of induction and dielectric measurements, and to diagnose fracture density; estimating volume fraction of isolated vuggy porosity for improving resistivity interpretation.

Figure 11:
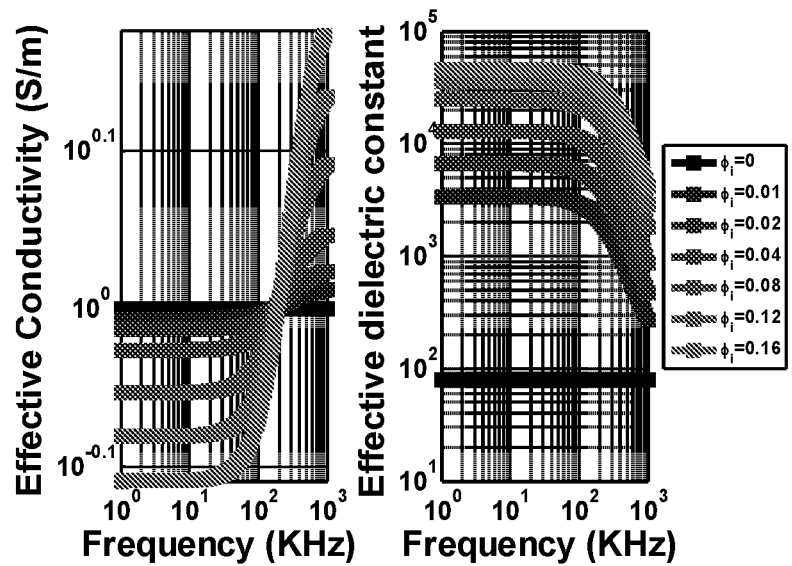
FIG. 11 shows a pair of graphs for the effect of volume fraction of spherical inclusion.
Figure 12:
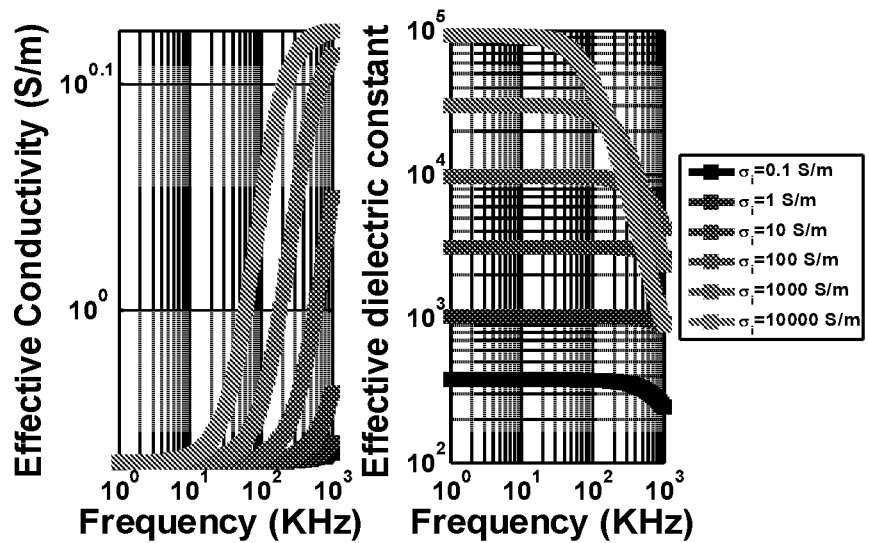
FIG. 12 shows a pair of graphs showing the effect of conductivity of spherical inclusion.
Figure 13:
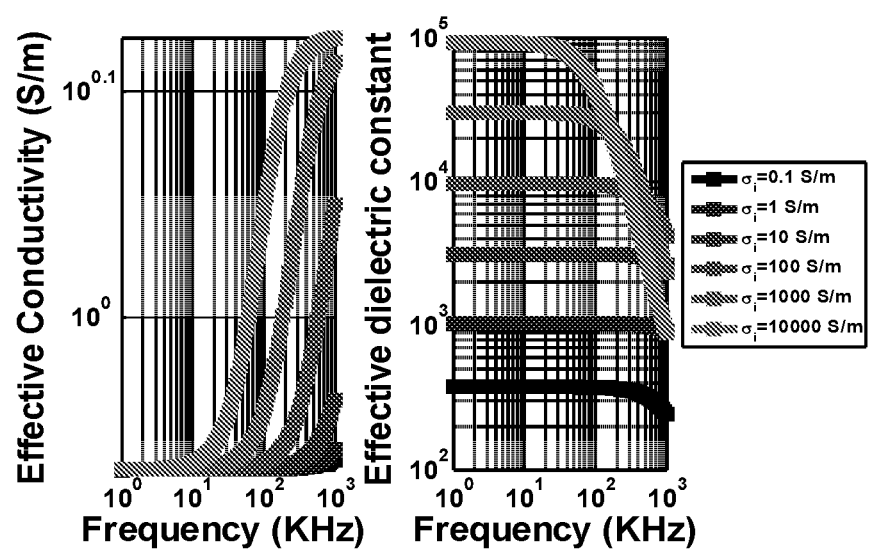
FIG. 13 shows a pair of graphs showing the effect of conductivity of a spherical inclusion.

A first case is shown in FIGS. 1 through 13, wherein dispersed highly-conductive spherical inclusion in an electrolyte-filled porous conductive medium. FIG. 11 shows the effect of volume fraction of spherical inclusion. FIG. 12 shows the effect of conductivity of spherical inclusion. FIG. 13 shows the effect of conductivity of a spherical inclusion.

Figure 14:
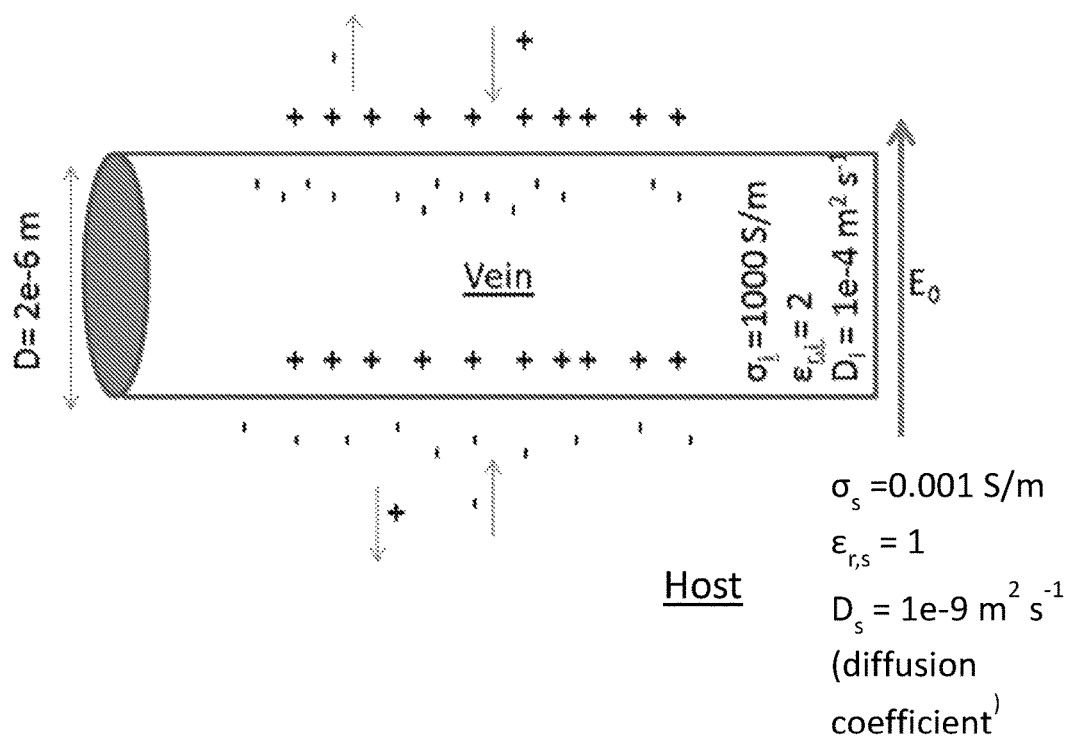
FIG. 14 shows a model of dispersed highly-conductive cylindrical veins in an electrolyte-filled porous low-conductivity medium is considered.
Figure 15:
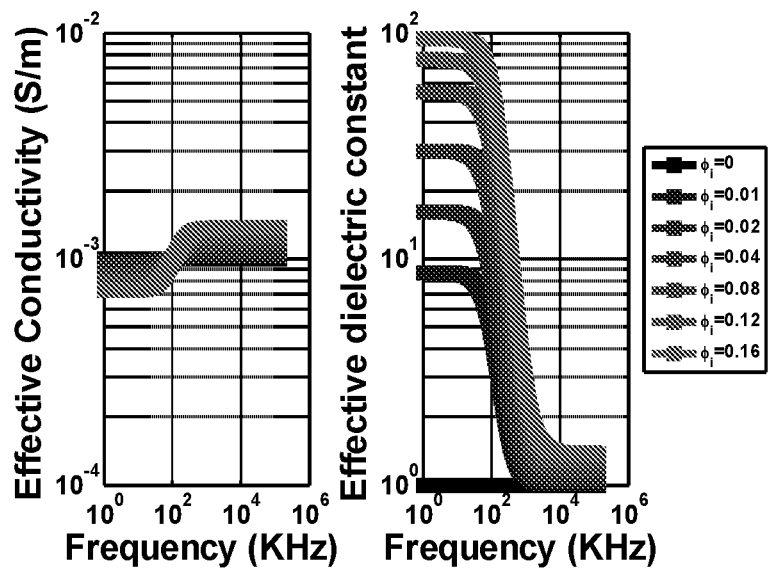
FIG. 15 shows a pair of graphs the effect of volume fraction of cylindrical veins of FIG. 14.
Figure 16:
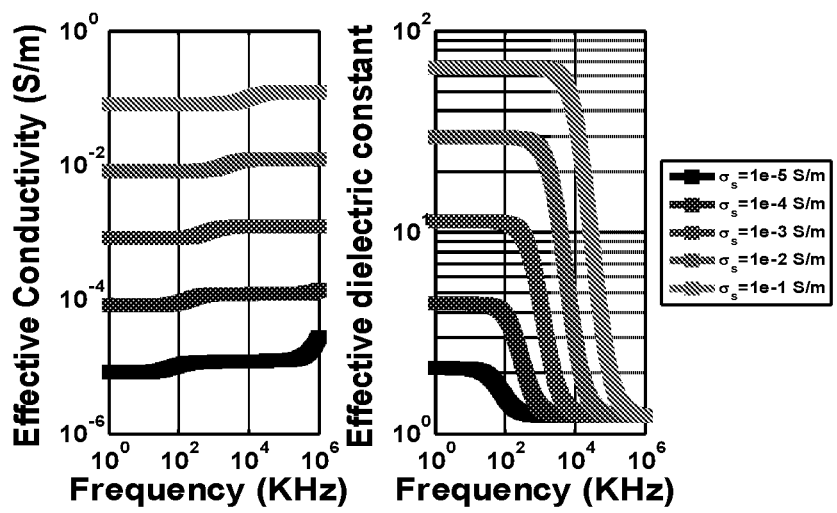
FIG. 16 shows a pair of graphs that shows the effect of conductivity of a host.
Figure 17:
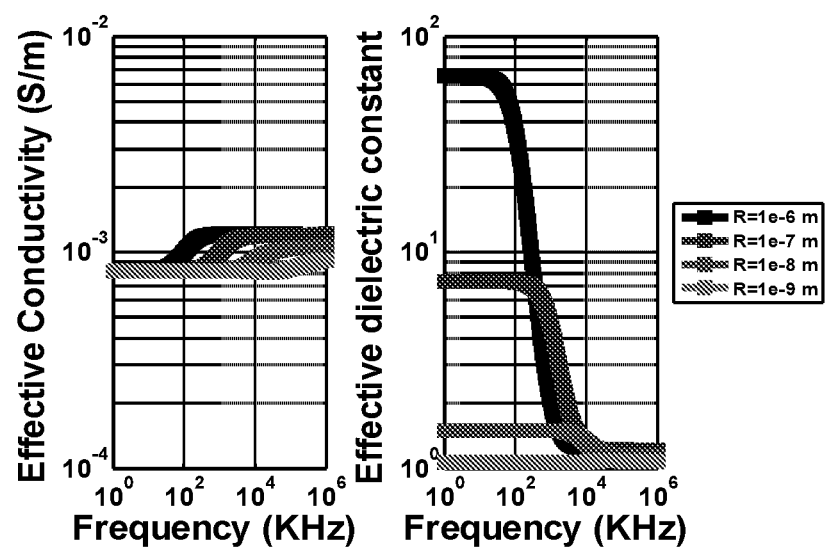
FIG. 17 shows a pair of graphs that show the effect of radius of cylindrical veins.

A second case is shown in FIGS. 14-15, wherein dispersed highly-conductive cylindrical veins in an electrolyte-filled porous low-conductivity medium is considered. FIG. 15 shows the effect of volume fraction of cylindrical veins. FIG. 16 shows the effect of conductivity of the host. FIG. 17 shows the effect of radius of cylindrical veins.

While the claimed subject matter has been described with respect to a limited number of embodiments, those skilled in the art, having benefit of this disclosure, will appreciate that other embodiments can be devised which do not depart from the scope of the claimed subject matter as disclosed herein. Accordingly, the scope of the claimed subject matter should be limited only by the attached claims.

What is claimed is:

1. A method to estimate water saturation in electromagnetic (EM) measurements comprising:
   making an EM measurement;
   performing at least one of creating an analytical forward model of the EM measurement, creating a numerical finite difference forward model of the EM measurement, performing an inversion;
   removing at least one petrophysically-adverse alteration of EM measurements in a frequency range from 1 Hz to 100 MHz; and
   wherein the at least one petrophysically-adverse alteration is due to the presence of at least one of the following: pyrite, graphitic-precursors, magnetite, and other conductive minerals.

2. The method according to claim 1, further comprising placing an arrangement of sensors into a wellbore environment for making the EM measurement.

3. The method according to claim 2, wherein the EM measurement is made of at least one of disseminated conductive/non-conductive vugs, veins, fractures, lamentations, and thin beds.

4. The method according to claim 1, wherein a joint interpretation is conducted on the volume fraction and geometry of conductive minerals.

5. A method, comprising:
  placing a wellbore tool in a wellbore to conduct a subsurface assessment of presence of conductive mineralization in hydrocarbon-bearing, mudrock, source rock, carbonate, and sedimentary formations;
  making an Electro Magnetic (EM) measurement;
  performing at least one of creating an analytical forward model of the EM measurement, creating a numerical finite difference forward model of the EM measurement, performing an inversion;
  removing at least one petrophysically-adverse alteration of EM measurements in a frequency range from 1 Hz to 100 MHz; and
  wherein the at least one petrophysically-adverse alteration is due to the presence of at least one of the following: pyrite, graphitic-precursors, magnetite, and other conductive minerals.

6. The method according to claim 2, wherein the EM measurement is made of at least one of disseminated conductive/non-conductive vugs, veins, fractures, lamentations, and thin beds.

7. The method according to claim 1, wherein the model satisfies the Kronig-Kramers relationship.

8. The method according to claim 5, wherein the model satisfies the Kronig-Kramers relationship.

* * * * *